United States Patent
Wang et al.

(10) Patent No.: US 10,024,827 B1
(45) Date of Patent: Jul. 17, 2018

(54) METHOD FOR SIMULTANEOUSLY DETECTING FOUR ISOMERS OF RESVERATROL IN PEANUT

(71) Applicant: Institute of Food Science and Technology, Chinese Academy of Agricultural Sciences, Beijing (CN)

(72) Inventors: Qiang Wang, Beijing (CN); Hui Hu, Beijing (CN); Xiaoyong Xia, Beijing (CN); Aimin Shi, Beijing (CN); Hongzhi Liu, Beijing (CN); Li Liu, Beijing (CN); Bo Jiao, Beijing (CN)

(73) Assignee: Institute of Food Science and Technology, Chinese Academy of Agricultural Sciences, Haidian District, Beijing (CN)

( * ) Notice: Subject to any disclaimer, the term of this patent is extended or adjusted under 35 U.S.C. 154(b) by 0 days.

(21) Appl. No.: 15/845,229

(22) Filed: Dec. 18, 2017

Related U.S. Application Data

(63) Continuation of application No. 15/790,127, filed on Oct. 23, 2017.

(30) Foreign Application Priority Data

Jul. 5, 2017 (CN) .......................... 2017 1 0543248

(51) Int. Cl.
*G01N 30/06* (2006.01)
*G01N 33/02* (2006.01)
(Continued)

(52) U.S. Cl.
CPC ............ *G01N 30/06* (2013.01); *G01N 30/34* (2013.01); *G01N 30/36* (2013.01); *G01N 33/02* (2013.01);
(Continued)

(58) Field of Classification Search
CPC ............ G01N 30/06; G01N 2030/062; G01N 2030/027; G01N 30/36; G01N 30/34
See application file for complete search history.

(56) References Cited

U.S. PATENT DOCUMENTS

2005/0266143 A1* 12/2005 Resurreccion ............ A23L 5/32
426/632

OTHER PUBLICATIONS

Goncalves, Joao et al., "New method for determination of (E)-resveratrol in wine based on microextraction using packed sorbent and ultra-performance liquid chromatography," J. Sep. Sci. 2011, 34, 2376-2384.*

(Continued)

*Primary Examiner* — Paul West
(74) *Attorney, Agent, or Firm* — Panitch Schwarze Belisario & Nadel LLP

(57) ABSTRACT

The present application relates to a method for simultaneously detecting four isomers of resveratrol in peanut by using ultra performance liquid chromatography during the operation procedure and accurately controlling the detection conditions. The method of the invention can achieve continuous sample injection, and perform sample analysis in batch. The detection time for each sample is only about 10 min, which greatly improves the detection efficiency. Further, the ultra performance liquid chromatography has high sensitivity and a low detection limit. The method of the invention adopts ethanol extraction under heating in the earlier stage of extraction, and controls the temperature of the extraction, so as to achieve effective extraction of four isomers of resveratrol, time saving, and efficient extraction and separation.

7 Claims, 6 Drawing Sheets

(51) Int. Cl.
  *G01N 30/34* (2006.01)
  *G01N 30/36* (2006.01)
  G01N 30/30 (2006.01)
  G01N 30/02 (2006.01)

(52) U.S. Cl.
  CPC . *G01N 2030/027* (2013.01); *G01N 2030/062* (2013.01); *G01N 2030/3007* (2013.01)

(56) References Cited

OTHER PUBLICATIONS

Berry, Judy et al., "UHPLC of Polyphenols in Red Wine," Application Note from Agilent Technologies, Inc., Apr. 23, 2010.*

* cited by examiner

METHOD FOR SIMULTANEOUSLY DETECTING FOUR ISOMERS OF RESVERATROL IN PEANUT

CROSS-REFERENCE TO RELATED APPLICATION

This application is a continuation of U.S. patent application Ser. No. 15/790,127 filed Oct. 23, 2017, which claims priority from Chinese Patent Application No. 201710543248.6, filed Jul. 5, 2017, the entire contents of the aforementioned applications are incorporated herein by reference.

TECHNICAL FIELD

The present invention relates to the field of detection of active substances in foods, specifically, to a method for simultaneously detecting the contents of four isomers of resveratrol and its glycosides in peanuts.

BACKGROUND ART

Resveratrol is a plant antitoxin generated by plants when they suffer pathogenic aggression and environmental deterioration. It is mainly derived from the plants such as peanuts, grapes, *Polygonum cuspidatum*, mulberry and the like. There are four forms of resveratrol in nature: trans-resveratrol, cis-resveratrol, trans-resveratrol glucoside and cis-resveratrol glucoside. Studies have shown that resveratrol is predominantly in trans form, trans-resveratrol and trans-resveratrol glucoside are thermally stable, and cis-resveratrol and cis-resveratrol glucoside are thermally unstable. Multiple studies have shown that the biological activity of trans-resveratrol is higher than that of cis-resveratrol, resveratrol glucoside is capable of releasing resveratrol under the action of glycosidase in human intestinal tract, and trans-isomer can be transformed into its cis-isomer under ultraviolet irradiation, thus, the establishment of an accurate method for determining four isomers of resveratrol in peanut is of great significance to detailed tracking studies of the transformation and loss of resveratrol and its glycosides during peanut processing, to the grasp of the loss law of resveratrol and its glycosides during the processing, and to the promotion of the development of resveratrol industry.

The molecular structures of the four isomers of resveratrol and its glycosides are shown as follows:

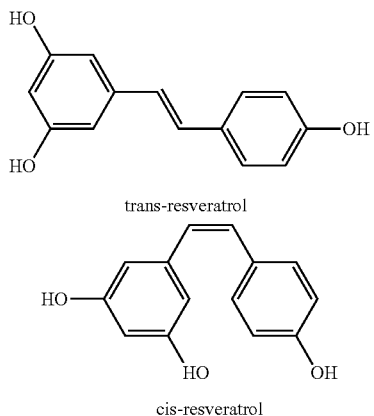
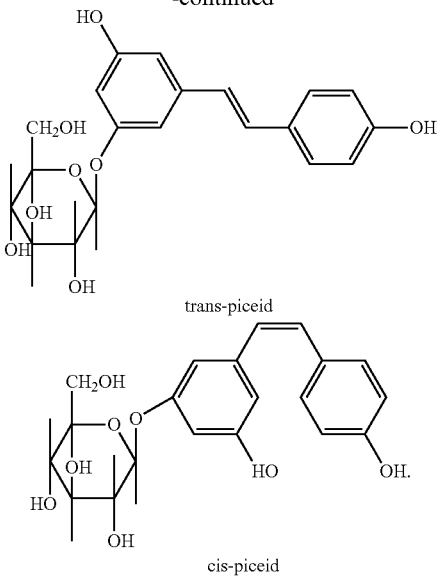

Resveratrol has very important application prospect. It has been found in studies that, resveratrol and resveratrol glucoside have variety of pharmacological effects; resveratrol can treat the anaphylactic diseases such as tinea and dermatitis, and has the effects of reducing lipid in serum and liver, preventing atherosclerosis, reducing platelet aggregation, protecting liver, and preventing coronary heart disease. In addition, resveratrol can effectively inhibit cell activity related with various processes of cancer. Furthermore, resveratrol, as a natural antioxidant, has been listed in "Anti-aging Scripture" (USA) as one of the "100 most popular effective anti-aging substances".

With the deep development of peanut, it is found that all parts of peanut have a relatively high content of resveratrol, for example, peanut sprout contains four isomers of resveratrol, peanut skin contains three isomers of resveratrol, and peanut butter contains one isomer of resveratrol. Therefore, it can lay a good foundation for the subsequent development of resveratrol resources to develop a method for extracting resveratrol from peanut quickly and efficiently and detecting the contents of the four structures of resveratrol and its glycosides in peanut simply, quickly and accurately.

There are many methods for detecting resveratrol, mainly including high performance liquid chromatography, gas chromatography-mass spectrometry and capillary electrophoresis.

1. High Performance Liquid Chromatography (HPLC)

At present, the most widely used method for quantitative analysis of resveratrol is high performance liquid chromatography which has the advantages of good reproducibility, high selectivity, high sensitivity and reliable results. HPLC can be used not only for the routine analysis of resveratrol, but also for the trace analysis of resveratrol in wine. However, HPLC requires long detection time, the amount of the analyzed sample is limited, and HPLC cannot be used for sample analysis on a large scale.

2. Gas Chromatography-Mass Spectrometry (GC/MS)

Gas chromatography-mass spectrometry (GC/MS) is carried out as follows: the sample is extracted with solid phase extraction cartridge and eluted with diethyl acetate, the eluent was blow-dried with $N_2$, derivatized with silanization reagent and then introduced into GC/MS instruments for analysis and detection.

The advantages of GC/MS comprise: simultaneous detection of cis-resveratrol and trans-resveratrol, less sample consumption (only 1 mL), high detecting speed (about 16 minutes), and low detection limit (minimum 3.72 μg/L). However, this method requires derivatization of the sample by silanization, which not only increases the processing links, but also leads to a higher determination result of cis-resveratrol and a lower determination result of trans-resveratrol relative to their actual contents.

3. Capillary Zone Electrophoresis (CZE)

Capillary zone electrophoresis (CZE) is also known as capillary free zone electrophoresis. As a rapidly-developing detection method in recent years, it was also applied in the detection of resveratrol. When resveratrol is analyzed by capillary zone electrophoresis, due to the polyhydroxy structure of resveratrol, it is easier to cause the adsorption of the sample, resulting in poor reproducibility. If the UV detector is adopted, due to the short optical distance of capillary zone electrophoresis, it may result in lower detection sensitivity, which is hard to reach μm level.

The detection of resveratrol has been developed in the direction of being more convenient, faster and more comprehensive. Therefore, on the basis of guaranteeing the authenticity of the method, it is necessary to provide a method to overcome the problems of the methods commonly used in the prior art, such as long detection time, low analysis efficiency, low sensitivity and poor reproducibility.

SUMMARY OF THE INVENTION

The present application provides a method for quickly and accurately detecting resveratrol in peanuts by using ultra performance liquid chromatography, in view of the existing problems in the detection process of resveratrol in peanut, such as long detection time, low analysis efficiency, low sensitivity and poor reproducibility and the like.

The method of the invention comprises the steps of:

1) the sample to be tested is subjected to pretreatment; and 2) the pretreated sample to be tested is detected by using ultra performance liquid chromatography under the following chromatographic conditions: $C_{18}$ column, PDA detector, a column temperature controlled at 33 to 38° C., and a detection wavelength of 285 nm for 2D and of 210 to 400 nm for 3D;

wherein the mobile phase is methanol (B) and 0.1% aqueous solution of formic acid (D);

the elution conditions are as follows: 0 min: 10% B, 90% D; 0.5 min: 10% B, 90% D; 2 min: 25% B, 75% D; 3.5 min: 30% B, 70% D; 4 min: 35% B, 65% D; 5 min: 50% B; 50% D; 7 min: 90% B, 10% D; 7.2 min: 10% B, 90% D; 10 min: 10% B, 90% D; and the flow rate of the mobile phase is 0.4 to 0.5 mL/min.

The invention adopts the ultra performance liquid chromatography (UPLC) to detect the sample to be tested, and the four isomers of resveratrol in the sample to be tested can be effectively separated and quickly detected by adjusting the composition of the mobile phase and the detection conditions. The above-described detection method of the four isomers is not limited to the detection of resveratrol from peanut, and it can also achieve the detection of four isomers of resveratrol from other sources.

Preferably, the sample to be tested comprises a fresh sample to be tested, a dry sample to be tested and a sample to be tested directly.

The fresh sample to be tested includes peanut sprout or peanut skin; the dry sample to be tested includes peanut root or peanut kernel; and the sample to be tested directly includes peanut butter.

Preferably, the pretreatment of the fresh sample to be tested or the dry sample to be tested comprises the steps of:

1) the fresh sample to be tested or the dry sample to be tested is dried to a moisture content of less than 5%;

2) the dried sample is crushed and sieved with a 60 mesh sieve;

3) the sieved and powdered sample is placed in 80% ethanol extracting solution and extracted under vibration at 70 to 80° C. in a constant-temperature water bath for 40 to 50 min; and 4) the mixture obtained from the extraction step is subjected to centrifugation, and the supernatant is filtered with a 0.2 to 0.25 um filter membrane, to obtain a pretreated sample to be tested;

and/or the pretreatment of the sample to be tested directly comprises the steps of:

1) the sample to be tested is placed in 80% ethanol extracting solution and extracted under vibration at 70 to 80° C. in a constant-temperature water bath for 40 to 50 min; and 2) the mixture obtained from the extraction step is subjected to centrifugation, and the supernatant is filtered with a 0.2 to 0.25 μm filter membrane, to obtain a pretreated sample to be tested.

Preferably, the drying method for the fresh sample to be tested is lyophilization by lyophilizer; and the drying method for the dry sample to be tested is carried out by placing the dry sample in a blast air oven and oven-drying at 50 to 60° C.

In the lyophilizing process, lyophilization at −50 to −55° C. for 45 to 50 hours is preferred with optimal effect.

In the oven-drying process, oven-drying at 55° C. is preferred with optimal effect.

0.22 μm filter membrane is commonly used, and effective protection of resveratrol can be provided by performing the whole pretreatment process under the condition of avoiding direct exposure to sunlight.

Preferably, the extraction method comprises the steps of:

1. Pretreatment of samples 1) the fresh sample to be tested or the dry sample to be tested is dried to a moisture content of less than 5%;

2) the dried sample is crushed and sieved with a 60 mesh sieve;

3) the sieved and powdered sample is placed in 80% ethanol extracting solution and is extracted under vibration at 130 to 150 r/min for 45 to 50 min in a constant-temperature water bath at 80° C., the mass-volume ratio of the sample to the ethanol extracting solution is 1-1.5:50; and 4) the mixture obtained from the extraction step is subjected to centrifugation, and the supernatant is filtered with a 0.22 μm filter membrane, to obtain a pretreated sample to be tested;

and/or the pretreatment of the sample to be tested directly comprises the steps of:

1) the sieved and powdered sample is placed in 80% ethanol extracting solution and extracted under vibration at 130 to 150 r/min for 45 to 50 min in a constant-temperature water bath at 80° C., the mass-volume ratio of the sample to the ethanol extracting solution is 1-1.5:50; and 2) the mixture obtained from the extraction step is subjected to centrifugation, and the supernatant is filtered with a 0.22 μm filter membrane, to obtain a pretreated sample to be tested.

Preferably, in the detection process, the column temperature is 35° C.

Preferably, in the detection process, the flow rate of the mobile phase is 0.45 mL/min.

Preferably, in the process of detection by ultra performance liquid chromatography, the C18 column is Waters ACQUITY UPLC HSS C18 column (2.1 mm×100 mm, 1.8 μm).

Preferably, the PDA detector is an Acquity UPLC PDA detector.

Preferably, the ultra performance liquid chromatograph is Waters ACQUITY UPLC H-CLASS.

Preferably, during the detection of resveratrol in a peanut sample, the method of the present invention comprises the steps of:

1. Pretreatment of samples 1) the fresh sample to be tested or the dry sample to be tested is dried to a moisture content of less than 5%;

2) the dried sample is crushed and sieved with a 60 mesh sieve;

3) the sieved and powdered sample is placed in 80% ethanol extracting solution and extracted under vibration at 130 to 150 r/min for 45 to 50 min in a constant-temperature water bath at 80° C., the mass-volume ratio of the sample to the ethanol extracting solution is 1-1.5:50; and 4) the mixture obtained from the extraction step is subjected to centrifugation, and the supernatant is filtered with a 0.22 μm filter membrane, to obtain a pretreated sample to be tested;

and/or the pretreatment of the sample to be tested directly comprises the steps of:

1) the sieved and powdered sample is placed in 80% ethanol extracting solution and extracted under vibration at 130 to 150 r/min for 45 to 50 min in a constant-temperature water bath at 80° C., the mass-volume ratio of the sample to the ethanol extracting solution is 1-1.5:50; and 2) the mixture obtained from the extraction step is subjected to centrifugation, and the supernatant is filtered with a 0.22 um filter membrane, to obtain a pretreated sample to be tested.

2. Detection of samples

The pretreated samples to be tested was detected by using ultra performance liquid chromatography, under the following chromatographic conditions: a $C_{18}$ column, a PDA detector, a column temperature controlled at 33 to 38° C., and a detection wavelength of 285 nm for 2D and of 210 to 400 nm for 3D;

wherein the mobile phase is methanol (B) and 0.1% aqueous solution of formic acid (D);

elution conditions are as follows: 0 min: 10% B, 90% D; 0.5 min: 10% B, 90% D; 2 min: 25% B, 75% D; 3.5 min: 30% B, 70% D; 4 min: 35% B, 65% D; 5 min: 50% B; 50% D; 7 min: 90% B, 10% D; 7.2 min: 10% B, 90% D; 10 min: 10% B, 90% D; and the flow rate of the mobile phase is 0.45 mL/min.

In the detection process, the ultra performance liquid chromatograph is Waters ACQUITY UPLC H-CLASS, the $C_{18}$ column is Waters ACQUITY UPLC HSS $C_{18}$ column (2.1 mm×100 mm, 1.8 μm), and the PDA detector is an Acquity UPLC PDA detector. The effective separation of four isomers can be achieved by the above method.

The above method can be used to extract resveratrol present in any part of peanut to a maximum extent and to maintain the activity of the extract, thereby achieving accurate detection and separation and obtaining a large quantity of high purity products.

The method of the present invention is also capable of achieving the quantitative detection of the four isomers of resveratrol in the sample to be tested, which comprises the step of:

A. standard substances of trans-resveratrol, trans-resveratrol glucoside, cis-resveratrol and cis-resveratrol glucoside in different concentrations are injected into $C_{18}$ column respectively, and detected by the method of step 2), standard curves are plotted according to the concentrations and peak areas of the standard substances; and B. the peak areas of the sample to be tested measured in step 2) are substituted into the above-mentioned standard curves respectively to obtain the concentration of the corresponding substance in the sample to be tested, and then the contents of the four isomers of resveratrol in the sample to be tested are calculated.

The calculation is carried out according to the following formula:

$$C=(A-b)\times 1/a\times c\times 1/W\times 1/1000$$

wherein:

C=concentration of the isomer of resveratrol in the sample to be tested;

A=peak area of the isomer of resveratrol;

W=sample weight (g);

A=slope of the standard curve;

B=intercept of the standard curve;

C=dilution multiple.

The method of the present invention has the following advantageous effects:

1) Ethanol has been used for the extraction in existing methods, but the extraction time is longer than that of the present invention. The present invention shortens the extraction time and maximally retains the activity of the unstable substance of resveratrol by extraction under heating and controlling the concentration of acetic acid, and the temperature and time of the extraction. Compared with the existing technology, the solvent is environmentally friendly, the method is simple and quick, and the sample is pure and has less contamination to the instrument.

2) Due to the ultra performance liquid chromatography method used in the present application, continuous sample injection can be achieved, and samples can be analyzed in batches. The detection time for each sample is only about 10 min, which greatly improves the detection efficiency.

SPECIFIC MODES FOR CARRYING OUT THE EMBODIMENTS

The following examples are intended to illustrate the invention, but not to limit the scope of the invention.

Example 1

The present Example relates to a method for qualitative and quantitative detection of resveratrol in peanut sprout, comprising the steps of:

1. Pretreatment of the sample to be tested:
    1) some fresh peanut sprouts were placed in a lyophilizer to be lyophilized for 48 h;
    2) the lyophilized peanut sprouts were pulverized with a high-speed pulverizer, and sieved with a 60 mesh sieve, and then the powder is collected and stored at low temperature in dark;
    3) 1 g of powder of peanut sprouts was weighed accurately, and added into a 150 ml triangular flask with stopper, 50 ml ethanol solution (80%, v/v) was added, and then extraction was carried out in a constant temperature water bath oscillator (80° C., 140 r/min) for 45 min; and
    4) the extracting solution was centrifuged at 5000 rpm for 10 min, and the supernatant was passed though a 0.22 μm microfiltration membrane to obtain a sample to be tested, wherein exposure to sunlight was avoided in the whole process;

2. The sample to be tested was analyzed and detected by ultra performance liquid chromatography, the instrument conditions were as follows:

Liquid Phase Conditions:

Column: Waters ACQUITY UPLC HSS $C_{18}$ column (2.1 mm×100 mm, 1.8 μm); PDA detector, a column temperature of 35° C., a detection wavelength of 285 nm for 2D and of 210 to 400 nm for 3D; an injection volume of 1 an injection mode of autoinjection. The mobile phase was methanol (B) and 0.1% aqueous solution of formic acid (D), and the elution conditions were as follows: 0 min: 10% B, 90% D; 0.5 min: 10% B, 90% D; 2 min: 25% B, 75% D; 3.5 min: 30% B, 70% D; 4 min: 35% B, 65% D; 5 min: 50% B; 50% D; 7 min: 90% B, 10% D; 7.2 min: 10% B, 90% D; 10 min: 10% B, 90% D. The flow rate was 0.4 to 0.5 mL/min;

3. Quantitative detection the quantitative detection method comprised the following steps: standard curve method was used, and it comprised plotting a standard curve with the concentrations of the standard solutions as the X-axis (mg/L) and the peak areas as the Y-axis, and calculating the linear regression as follows:

trans-resveratrol y=8957.3x−2488 $R^2$=0.9999
trans-resveratrol glucoside y=4695.4x−1687.8 $R^2$=0.9997
cis-resveratrol y=6894.1x+32769 $R^2$=0.9989
trans-resveratrol glucoside y=4047.5x+4740.6 $R^2$=0.9979 to ensure that the linear relationship is good ($R^2$>0.997); the concentration of each isomer of resveratrol in the sample was calculated by the following formula (mg/kg):

$$C=(A-b)\times 1/a \times c \times 1/W \times 1/1000$$

wherein:
C=concentration of the isomer of resveratrol in the sample to be tested;
A=peak area of the isomer of resveratrol;
W=sample weight (g);
A=slope;
B=intercept;
C=dilution multiple.

Figure 1:
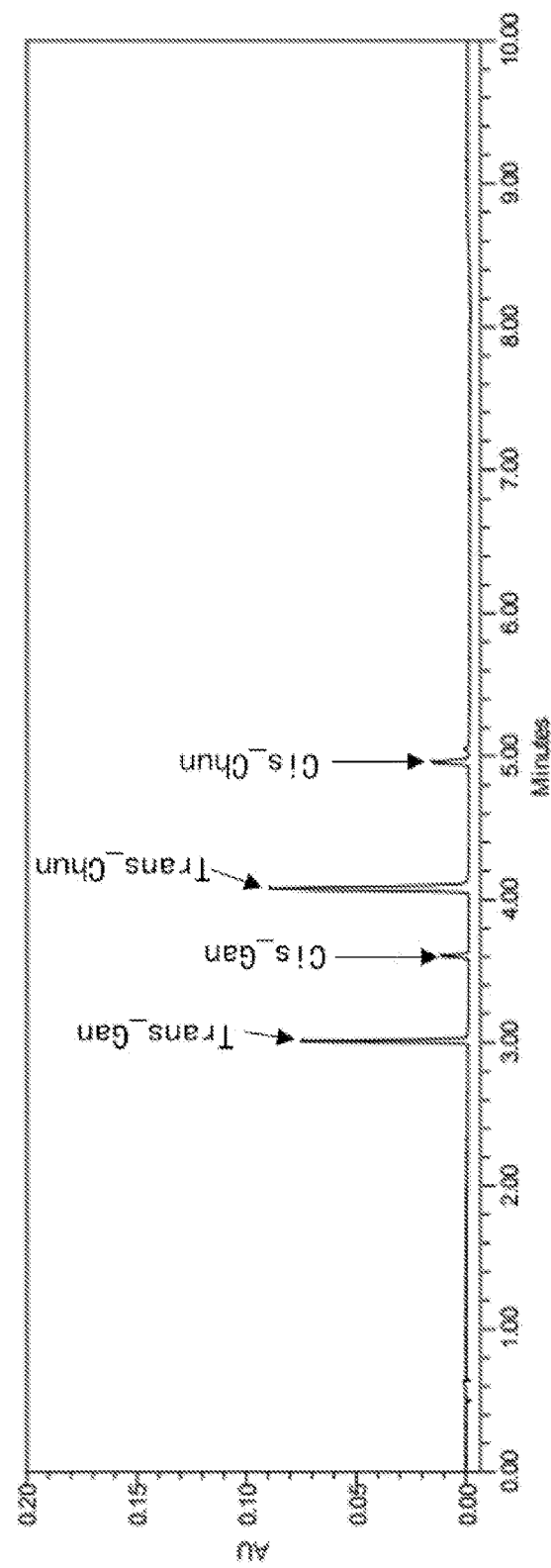
FIG. 1 shows the UPLC spectrum of four isomers of resveratrol.
Figure 2:
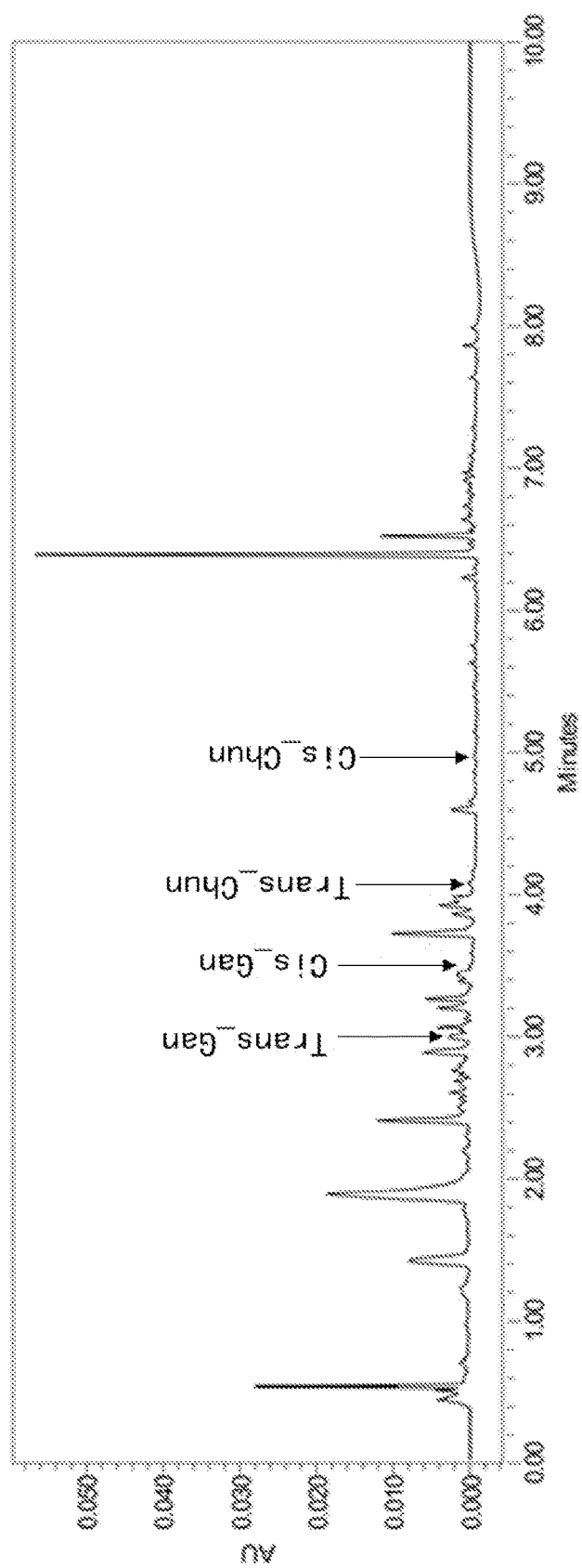
FIG. 2 shows the UPLC spectrum of four isomers of resveratrol in peanut sprout.

In order to judge the appearance time of the four isomers, standard samples were introduced to obtain FIG. 1. The sample was detected to obtain the chromatogram as shown in FIG. 2, the content of trans-resveratrol (trans-Chun) in the peanut sprout sample was calculated to be 0.030 mg/kg, the content of trans-resveratrol glucoside (trans-Gan) was 0.099 mg/kg, the content of cis-resveratrol (cis-Chun) was 0.025 mg/kg, and the content of cis-resveratrol glucoside (cis-Gan) was 0.049 mg/kg.

Example 2

The present Example relates to a method for qualitative and quantitative detection of resveratrol in peanut skin, comprising the steps of:

1. Pretreatment of the sample to be tested:
    1) some peanut skin samples were oven-dried in a blast air oven at 55° C. for 9 h;
    2) the treated peanut skins were pulverized by a high-speed pulverizer, and sieved with a 60 mesh sieve, and then the powder was collected and stored at low temperature in dark;
    3) 1 g peanut skin powder was weighed accurately, and added into a 150 ml triangular flask with stopper, 50 ml ethanol solution (80%, v/v) was added, and then extraction was carried out in a constant temperature water bath oscillator (80° C., 140 r/min) for 45 min; and
    4) the extracting solution was centrifuged at 5000 rpm for 10 min, the supernatant was passed though a 0.22 μm microfiltration membrane to obtain a sample to be tested, wherein exposure to sunlight was avoided in the whole process.

The steps of instrumental analysis and data processing were the same as those in Example 1.

Figure 3:
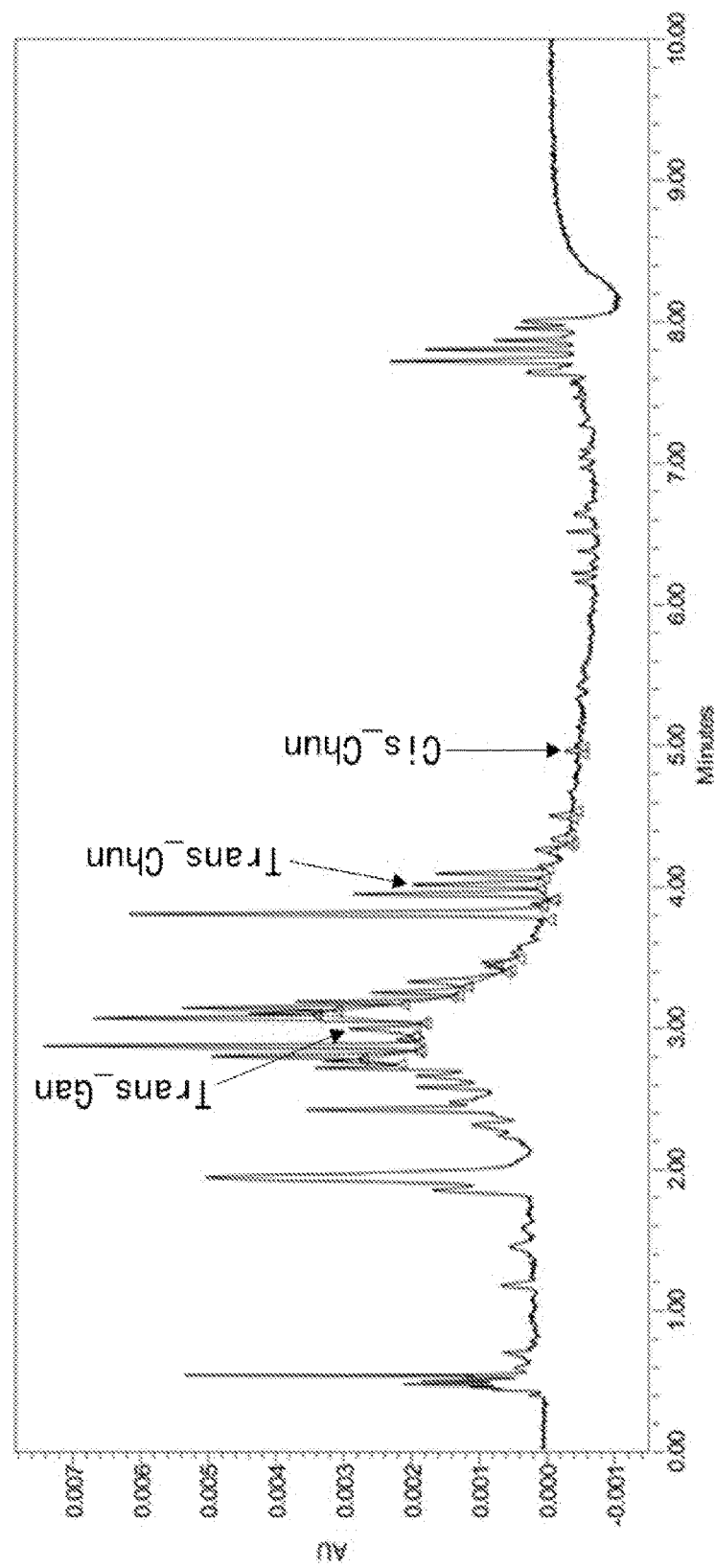
FIG. 3 shows the UPLC spectrum of three isomers of resveratrol in peanut skin.

The obtained chromatogram was shown in FIG. 3. The content of trans-resveratrol (trans-Chun) in the peanut skin sample was calculated to be 1.492 mg/kg, the content of trans-resveratrol glucoside (trans-Gan) was 0.073 mg/kg, the content of cis-resveratrol (cis-Chun) was 0.489 mg/kg, and cis-resveratrol glucoside (cis-Gan) was not detected.

Example 3

The present Example relates to a method for qualitative and quantitative detection of resveratrol in peanut butter, comprising the steps of:

1) 1 g peanut butter sample was weighed accurately, and added into a 150 ml triangular flask with stopper, 50 ml ethanol solution (80%, v/v) was added, and then extraction was carried out in a constant temperature water bath oscillator (80° C., 140 r/min) for 45 min; and
2) the extracting solution was centrifuged at 5000 rpm for 10 min, the supernatant was passed though a 0.22 μm microfiltration membrane to obtain a sample to be tested, wherein exposure to sunlight was avoided in the whole process.

The steps of instrumental analysis and data processing were the same as those in Example 1.

Figure 4:
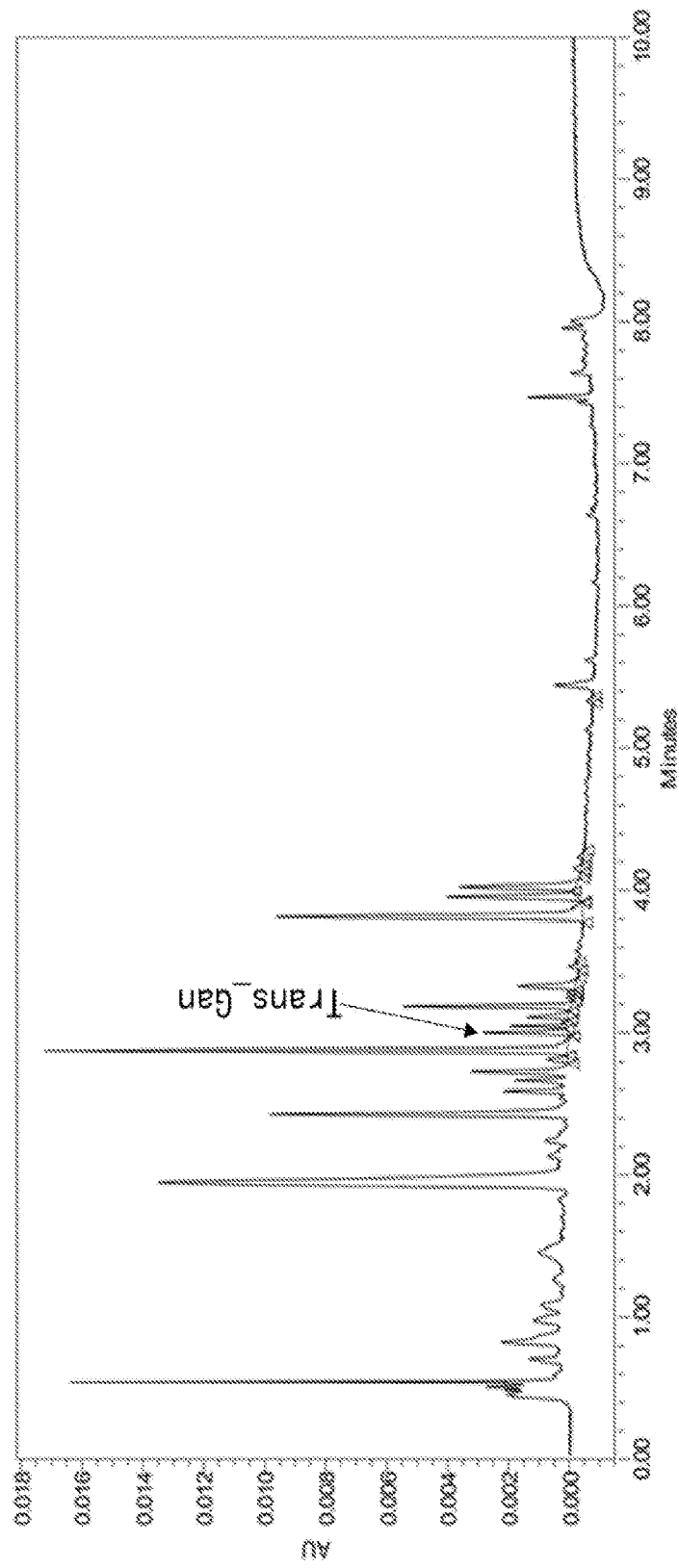
FIG. 4 shows the UPLC spectrum of one isomer of resveratrol in peanut butter.

The obtained chromatogram was shown in FIG. 4, the content of trans-resveratrol glucoside (trans-Gan) in the peanut butter sample was calculated to be 2.572 mg/kg, and trans-resveratrol (trans-Chun), cis-resveratrol (cis-Chun) and cis-resveratrol glucoside (cis-Gan) were not detected.

Comparative Example 1

Figure 5:
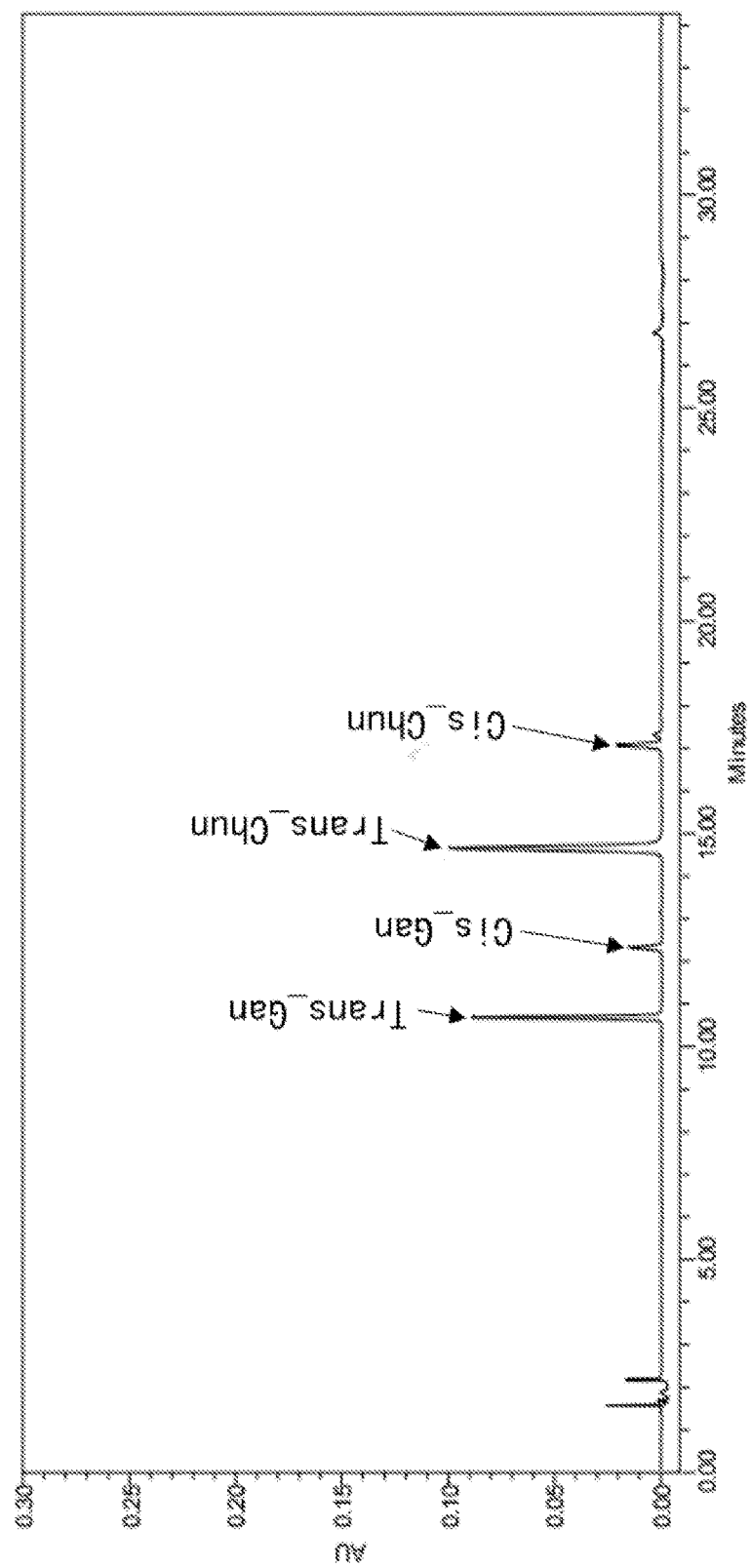
FIG. 5 shows the HPLC spectrum of four isomers of resveratrol.

By using high performance liquid chromatography instead of ultra performance liquid chromatography for detection, the actually measured appearance time of standard samples of the four isomers of resveratrol were as follows: trans-resveratrol at 14.663 min, cis-resveratrol at 17.069 min, trans-resveratrol glucoside at 10.681 min, and cis-resveratrol glucoside at 12.326 min, as shown in FIG. 5.

In addition, the whole process of sample detection needs 35 min, whereas the ultra performance liquid chromatography of the present invention only needs 10 min.

Comparative Example 2

Compared with Example 2, the difference of the comparative example 2 lied in that peanut skin was detected, and the pretreatment method thereof was as follows: 3 g peanut skin was weighed accurately, placed in a 150 ml triangular flask with stopper, added with 45 ml of absolute ethanol with a volume fraction of 75%, ultrasonically extracted at 50° C. for 64 min, and then centrifuged at 5000 r/min for 10 min; and the supernatant was sieved with a 0.22 μm filter membrane to give a sample to be tested.

Figure 6:
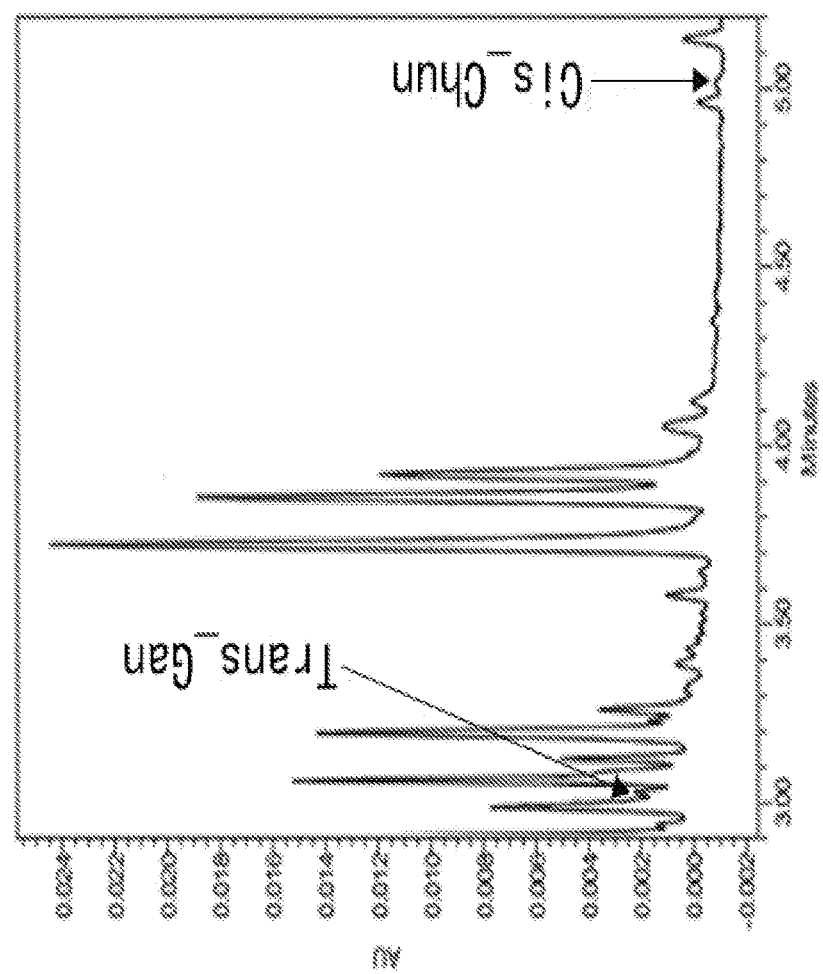
FIG. 6 shows the UPLC spectrum of resveratrol extracted from peanut skin by the method described in the Comparative Example.

Only two active ingredients could be detected in the sample prepared by the above method, as shown in FIG. 6, and the ingredients were trans-resveratrol glucoside (trans-Gan) and cis-resveratrol (cis-Chun), respectively. It is further demonstrated that the pretreatment method described in the present invention can be used to extract the resveratrol sufficiently.

In the drawings of the present invention, there is a portion where the characters and the spectrum overlap. Since the appearance time determines the type of the substance, clear disclosure is not affected even if the characters overlap the spectrum.

While the present invention has been described in detail by way of general description, specific embodiments and tests, modifications and improvements that may be made without departing from the spirit of the invention are within the scope of the invention as claimed.

What is claimed is:

1. A method for simultaneously detecting four isomers of resveratrol in a sample to be tested, the method comprising the steps of:
   1) pretreating the sample to be tested to obtain a pretreated sample to be tested,
   2) detecting the four isomers of resveratrol from the pretreated sample to be tested using an ultra performance liquid chromatography method with a $C_{18}$ column having a column temperature controlled at 33 to 38° C., a photodiode array (PDA) detector having simultaneous detection wavelengths of 285 nm for 2-dimensional operation and 210 to 400 nm for 3-dimensional operation, and a mobile phase containing methanol (B) and 0.1% aqueous solution of formic acid (D), wherein the elution conditions for the method are as follows: 0 min: 10% B, 90% D; 0.5 min: 10% B, 90% D; 2 min: 25% B, 75% D; 3.5 min: 30% B, 70% D; 4 min: 35% B, 65% D; 5 min: 50% B; 50% D; 7 min: 90% B, 10% D; 7.2 min: 10% B, 90% D; and 10 min: 10% B, 90% D; and the flow rate of the mobile phase is 0.4 to 0.5 mL/min;
   wherein the sample to be tested is selected from the group consisting of a fresh sample, a dry sample and a third sample; and
   wherein the pretreatment of the fresh sample to be tested or the dry sample to be tested comprises the steps of:
   1) drying the fresh sample to be tested or the dry sample to be tested to a moisture content of less than 5%, to obtain a dried sample;
   2) crushing and sieving the dried sample with a 60 mesh sieve, to obtain a sieved and powdered sample;
   3) extracting the sieved and powdered sample with 80% ethanol extracting solution under vibration at 70 to 80° C. in a constant-temperature water bath until all of the resveratrol and its glycosides are dissolved in the ethanol extracting solution, to obtain a mixture; and
   4) centrifuging the mixture obtained from the extraction step to obtain a supernatant, and filtering the supernatant with a 0.2 to 0.25 μm filter membrane, to obtain a pretreated sample to be tested;
   and/or the pretreatment of the third sample to be tested comprises the steps of:
   1) extracting the third sample to be tested with 80% ethanol extracting solution under vibration at 70 to 80° C. in a constant-temperature water bath until all of the resveratrol and its glycosides are dissolved in the ethanol extracting solution, to obtain a mixture; and
   2) centrifuging the mixture obtained from the extraction step to obtain a supernatant, and filtering the supernatant with a 0.2 to 0.25 μm filter membrane, to obtain a pretreated sample to be tested.

2. The method according to claim 1, wherein the fresh sample to be tested comprises peanut sprout or peanut skin; the dry sample to be tested comprises peanut root or peanut kernel; and the third sample to be tested comprises peanut butter.

3. The method according to claim 1, wherein the drying method for the fresh sample to be tested is lyophilization by lyophilizer; and the drying method for the dry sample to be tested is oven-drying with hot air at a temperature of 50 to 60° C.

4. The method according to claim 1, wherein the column temperature is 35° C.

5. The method according to claim 1, wherein the flow rate of the mobile phase is 0.45 mL/min.

6. The method according to claim 1, wherein:
   a). in steps 3) and 4) of the pretreatment of the fresh sample to be tested or the dry sample to be tested:
      3) the sieved and powdered sample is placed in 80% ethanol extracting solution and extracted under vibration at 130 to 150 r/min for 45 to 50 min in a constant-temperature water bath at 80° C., wherein the mass-volume ratio of the sample to the ethanol extracting solution is 1-1.5:50, to obtain a mixture; and
      4) the mixture obtained from the extraction step is subjected to centrifugation, and the supernatant is filtered with a 0.22 μm filter membrane, to obtain a pretreated sample to be tested;
   b). in steps 1) and 2) of the pretreatment of the third sample to be tested:
      1) the third sample is placed in 80% ethanol extracting solution and extracted under vibration at 130 to 150 r/min for 45 to 50 min in a constant-temperature water bath at 80° C., wherein the mass-volume ratio of the sample to the ethanol extracting solution is 1-1.5:50, to obtain a mixture; and
      2) the mixture obtained from the extraction step is subjected to centrifugation, and the supernatant is filtered with a 0.22 um filter membrane, to obtain a pretreated sample to be tested;
   c). in the detection step of the one or more samples to be tested:
      the flow rate of the mobile phase is 0.45 mL/min.

7. The method according to claim 1, wherein the method further comprises performing quantitative detection of the four isomers of resveratrol using a method, comprising the steps of:

A. injecting standard substances of the four isomers of resveratrol selected from the group consisting of trans-resveratrol, trans-resveratrol glucoside, cis-resveratrol and cis-resveratrol glucoside in different concentrations into the $C_{18}$ column respectively, and detecting concentrations and peak areas of the standard substances by the ultra performance liquid chromatography method of claim 4, and plotting standard curves according to the detected concentrations and peak areas of the standard substances; and
B. substituting the peak areas of the four isomers of resveratrol from the sample to be tested measured in claim 4 into the standard curves respectively to obtain the concentrations of the corresponding substances in the sample to be tested, and calculating the contents of the four isomers of resveratrol in the sample to be tested.

* * * * *